US008459989B2

(12) United States Patent
Keski-Nisula et al.

(10) Patent No.: US 8,459,989 B2
(45) Date of Patent: Jun. 11, 2013

(54) ORTHODONTIC ACTIVATOR

(75) Inventors: Katri Keski-Nisula, Vaasa (FI); Juha Varrela, Turku (FI)

(73) Assignee: LM-Instruments Oy, Parainen (FI)

(*) Notice: Subject to any disclaimer, the term of this patent is extended or adjusted under 35 U.S.C. 154(b) by 0 days.

(21) Appl. No.: 12/836,181

(22) Filed: Jul. 14, 2010

(65) Prior Publication Data
US 2010/0279246 A1    Nov. 4, 2010

Related U.S. Application Data

(63) Continuation of application No. 10/563,894, filed as application No. PCT/FI2004/000434 on Jul. 7, 2004, now abandoned.

(30) Foreign Application Priority Data

Jul. 7, 2003 (FI) ........................ 20031038

(51) Int. Cl.
*A61C 3/00* (2006.01)

(52) U.S. Cl.
USPC ................................. 433/24; 433/6

(58) Field of Classification Search
USPC ............ 433/6, 24, 18, 19, 140, 215; 128/848, 128/859–862; D24/180
See application file for complete search history.

(56) References Cited

U.S. PATENT DOCUMENTS

| | | | |
|---|---|---|---|
| 2,833,278 A | 5/1958 | Ross | |
| 2,966,908 A | 1/1961 | Cathcart et al. | |
| 3,333,582 A * | 8/1967 | Cathcart | 128/862 |
| 3,939,598 A | 2/1976 | Bergersen | |
| 4,580,975 A | 4/1986 | Schrems et al. | |
| 4,784,605 A * | 11/1988 | Bergersen | 433/6 |
| 4,799,884 A | 1/1989 | Bergersen | |
| 4,830,612 A * | 5/1989 | Bergersen | 433/6 |
| 4,919,612 A | 4/1990 | Bergersen | |
| 5,037,295 A * | 8/1991 | Bergersen | 433/6 |
| 5,645,420 A * | 7/1997 | Bergersen | 433/6 |
| 5,666,974 A * | 9/1997 | Hiro et al. | 128/861 |
| 5,879,199 A | 3/1999 | Belopolsky | |
| 6,132,208 A | 10/2000 | Mathieu | |
| 6,837,246 B1 * | 1/2005 | DeLuke | 128/860 |
| 2003/0198911 A1 | 10/2003 | Knopp et al. | |
| 2003/0225594 A1 | 12/2003 | Bergersen | |

FOREIGN PATENT DOCUMENTS

| | | |
|---|---|---|
| EP | 0315777 | 5/1989 |
| FR | 2 786 089 | 5/2000 |
| FR | 1104897 | 4/2001 |
| WO | 02/062252 | 8/2002 |
| WO | 02/062253 | 8/2002 |
| WO | WO02062253 A1 * | 8/2002 |

OTHER PUBLICATIONS

Mechanical translation of FR 2 786 089, 6 pages.

* cited by examiner

Primary Examiner — Yogesh Patel
(74) Attorney, Agent, or Firm — Cozen O'Connor

(57) ABSTRACT

An odontological device to guide occlusion of an individual. The device contains a U-shaped arch with concaves on the side of both the lower jaw and the upper jaw. The bottom surfaces of the concaves form an isthmus separating the concaves from one another. The isthmus includes blanks for individual teeth and uniform, continuous hollows for at least two teeth. The lower jaw side of the device has a lower wing constricting a tongue at least sideways.

18 Claims, 3 Drawing Sheets

A - A

ORTHODONTIC ACTIVATOR

CROSS-REFERENCE AND RELATED APPLICATIONS

This application is a continuation of application Ser. No. 10/563,894 filed Jun. 1, 2006 now abandoned which is a National Phase application of PCT patent application No. PCT/FI 2004/000434, filed Jul. 7, 2004, the disclosures of which are incorporated herein.

The present invention concerns an odontological device for guiding the occlusion of an individual.

BACKGROUND OF THE INVENTION

This kind of device usually comprises a U-shaped arch that has a lower surface on the lower jaw side and an upper surface on the upper jaw side, both of which have teeth receiving concaves. The device is made of a flexible and elastic material, such as a thermoplastic elastomer, plasticized (softened) plastic or rubber or of a similar material.

The invention, furthermore, relates to an occlusion guidance device series as well as a method for selecting a device for occlusion guidance in orthodontic treatment. In the method, at least one characteristic measurement is defined for a person's teeth, and an appropriate device is selected for the person based on this measurement.

The treatment method by which to achieve the required occlusion is also described in the description of the invention.

Odontological occlusion guidance appliances, orthodontic braces and equivalent odontological devices are used fairly commonly to treat and eliminate problems such as supraocclusion, rotations and individual cross-bites. Previously known devices are dental braces made of steel and teeth positioning devices made of flexible materials. In the latter ones, i.e. the (so-called) occlusion guidance appliances, there are typically concaves for the teeth of the lower and upper jaw that are separated by an isthmus that has recesses, so-called "blanks", formed for the individual teeth. With these blanks individual teeth can be guided to the required place and position. Devices of a kind, where a part of said blanks has been replaced with compartments intended for more than one tooth, are also known. The devices have been designed and are meant to be used mainly during the phase when the milk teeth are being replaced by adult teeth and after the adult teeth have erupted. The occlusion guidance appliances are meant to be used passively, particularly during the night, but in difficult or complex cases they are recommended to be used also for 1-4 hours during the daytime. The manufacturing material in the known technology has normally been plasticized (softened) polyvinyl chloride.

Occlusion guidance appliances have been presented, for example, in published patent applications nos. WO 02/062253 and WO 02/062252, FR Patent Specification No. 1 104897 as well as in U.S. Pat. Nos. 4,784,605, 4,799,884, 4,830,612, 4,919,612 and 5,879,199, the contents of which are herewith incorporated by reference.

U.S. Pat. No. 4,830,612 presents an occlusion guidance appliance designed for children of ages 2-6, where the incisors, canine teeth and the first middle teeth each have their own blanks. A single, continuous and uniform compartment has then been formed for the second middle tooth and first molars. The device is meant to be used before the milk teeth come out and is appropriate only for the milk teeth, since the device ends before the second molar. In the description and the claims it has been emphasized that the device should at a maximum extend to the point where the first molar will erupt. This kind of device cannot be recommended for use by older children, because there is a danger that the second molar will over-erupt and cause an open occlusion. If one wants to continue the treatment of the patient even after the permanent teeth have erupted, the device must be replaced by another device designed for that phase of development. The use of many different kinds of occlusion guidance appliances will be expensive for the patient and will require the manufacturer and the dentist to have a wide range of products.

In addition to the above-mentioned problems, there are also other disadvantages related with the known solutions. Typically, it is difficult to get the occlusion guidance appliance to remain in the correct position in the mouth, for example, when the person is sleeping and the lower jaw very easily "drops" and retracts somewhat. This could lead to the patient biting the device from the inside of the lower edge, in which case the device is not working as it should, and is in fact guiding the positioning of teeth towards a different direction than originally intended. In addition, the device, if not properly positioned in the mouth, may be easily bitten during daily use to the point where it breaks.

In WO Publications Nos. 02/1062253 and 02/1062252 a device is disclosed, which is meant for positioning the teeth and in which the inner wall of the lower jaw side concave extends downwards in such a way that it forms a tongue ramp. This is designed to partially encircle the tongue from underneath. The publication has no mention of using the tongue ramp, for example, to further the stationary position of the occlusion guidance appliance.

Further, the problem in known solutions is that the occlusion guidance appliances have been designed to be used in a particular developmental phase of the teeth. In this case, the device to be used has to be chosen not only according to the size of the teeth but also from a variety of different devices. On top of the problems of selecting the device and the frequency of changing it, there is also the added costs arising from a need to maintain a large range of products.

OBJECTS AND SUMMARY OF THE INVENTION

It is an aim of the present invention to remove disadvantages associated with known technology and to create a completely new kind of way of treating the occlusion of a person. The objective of the invention is particularly to form an occlusion guidance appliance that will remain properly positioned in the mouth in different use environments and in different ways of use, including when being worn by small children. In addition, it is an aim to enable the guiding of the occlusion using an essentially similar-shaped device both in the milk tooth phase and in subsequent phases.

Furthermore, it is an objective to provide a series of occlusion guidance appliances that are appropriate for use in all developmental phases of the teeth, in which case the appropriate device can be chosen and/or it can be changed to another one, only on the basis of the size of the person's dental arch.

Thus, it is also an aim of the invention to provide a new method in orthodontics to be used for selecting the occlusion guidance appliance, one where the appropriate occlusion guidance appliance is easily selected, based on a simple measurement, from one type of device without having also to consider the developmental phase of the teeth.

The invention is based on the idea that treatment results can be improved by providing an occlusion guidance device with wings and other structures that ease the use of the device and particularly help to keep it stationary in the mouth. We have concluded that by forming these kinds of wings in a suitable manner we can also ensure that a person cannot gradually bite through the device while using it. With the shaping of the wings it is also possible to ensure that even teeth erupting very obliquely can be guided inside the device. In the orthodontic activator according to the invention it is thus essential that at least one wing is arranged to form a lower wing on the lower surface of the occlusion guidance appliance. This lower wing, which is formed as an extension of the inner/lingual side wall on lower jaw side concave in the device, constricts the tongue at least sideways. Advantageously, the device includes also a wing on the labial side of the upper teeth, suitably extending over the gum line.

The introduction of the device into the mouth and its use can also be facilitated, particularly if the device is further provided with uniform compartments for some of the teeth, instead of individual blanks. This can be done particularly in cases where the aim is mainly to align the teeth in the required place, rather than to precisely guide into a specific position. The use of compartments shared by more than one tooth will ease placing the device in the mouth, particularly in some cases where the occlusion is not correct, such as when the front tooth or teeth are twisted. However, according to the invention, it is not advantageous to use only one compartment along the length of the entire dental arch, since it is not possible to achieve the necessary precision required of the orthodontics to position the device correctly in the mouth merely with the aid of the wings and by having a correctly curved device.

In the orthodontic activator according to the invention, the isthmus interconnecting the concaves for the upper and lower jaw therefore contains uniform areas for one or more tooth groups. These shared areas include particularly compartment-like recesses. In addition to this, the device advantageously includes individual blanks at least for one tooth of each quarter of the teeth, and these blanks further the correct placement of the occlusion guidance appliance in relation to the teeth.

As a result of its structure, the device according to the invention is suitable for children of all ages, particularly those between 5 and 15 years. A device series intended for anatomies (dental arches) of different dimensions can be manufactured such that there is always a device of a suitable size available for any individual.

The series can be used in a method for selecting an occlusion guidance appliance to be employed in orthodontics. In this method, firstly at least one characteristic measurement of the individual's teeth is defined, and an appropriate device is selected for the individual from the series of occlusion guidance appliance devices based on this measurement. The invention is characterized in that the measurement is the length of the dental arch, which is measured from the upper jaw side dental arch on the left and right side, particularly between the second and third or possibly third and fourth teeth. Based on the resulting measurement a suitable occlusion guidance appliance device is selected.

More specifically. the odontological device according to the invention is characterized by including a wing on the lower jaw side of the device extending downward toward the bottom of the mouth cavity and essentially following the shape of the lower jaw.

The series of odontological devices can comprise a series of essentially conformed devices of different sizes, wherein the devices correspond to the odontological devices described above.

The method for selecting an occlusion guidance appliance device can include steps as follows:

at least one characteristic measurement is defined for an individual's teeth, and based on this measurement an appropriate device is selected for that individual, comprising the steps of:

measuring the length of the upper jaw side dental arch from the individual's teeth between the left and right hand side front and middle teeth or two middle teeth, choosing, based on the measurement without taking separately into consideration the developmental phase of the teeth, a suitable occlusion guidance appliance device from an occlusion guidance appliance device series, which contains several essentially conformal and different-sized occlusion guidance appliance devices.

By means of the invention and its preferred embodiments significant advantages can be achieved. In such a device, as a result of the combination of compartments, blanks and lower wings according to the invention, even small children can easily put the device in their mouths so that it is reliably in the correct place. The blanks position the device on to the teeth and the dental arch, the compartments reduce problems caused by twisted teeth when inserting the device in the mouth, for example, and the lower wings help to keep the device in place. Thanks to the lower wing construction, the device is more likely to remain intact because the wings prevent the front teeth biting together to the extent that they could cut through the device and in turn make it difficult to turn the device in the mouth, so that the possibility of biting through the edges is reduced.

In one preferred embodiment of the device, the upper lip side edge of the occlusion guidance appliance has been raised in such a way that it extends at least partially above the gum line. In this way, good guidance of the teeth is also obtained in difficult cases, and the device will sit more comfortably in the mouth.

According to one preferred embodiment of the invention, the groups of teeth have been provided with compartments particularly in the area of the first molar and at least partially in the area where the second molar will erupt. With this solution, open occlusion problems possibly caused by over-eruption of the second molar can be diminished or even prevented.

The invention enables the use of an occlusion guidance appliance with the same basic structure all the way from the milk tooth phase to the guiding of the occlusion of the permanent teeth. A series of essentially conforming devices will be made from the device, and in everyone of these the same basic solutions are used so that an appropriate device is chosen for the individual under treatment according to the length of the dental arch. In this context, "conforming" means that the devices have the same basic structure, they preferably have compartments, blanks and wings arranged with respect to the teeth recesses. The individual devices of the device series can also geometrically conform to each other, but this is not necessary when constructing a device series meant to treat occlusion.

A device according to the invention can be used both for milk teeth, changing teeth and permanent teeth. Thus, the cost of orthodontics is reduced when the patient is not required to use a new occlusion guidance appliance in each developmental phase of the teeth, rather the device needs to be replaced by a new one only as a result of dental arch growth.

The device according to the invention essentially works for everyone.

It can be used in treating both horizontal and vertical overbite as well as the narrowness of the front area and of rotations and individual cross-bites. In addition, a device according to one application form of the invention is also suitable for treating open occlusion.

The advantages of the uses of the embodiments of the invention have been described also in copending Finnish patent application (Purennanohjain ["Occlusion guidance appliance"]) filed at the same time with this application, and incorporated by reference.

BRIEF DESCRIPTION OF THE DRAWINGS

The invention and its other preferred embodiments will be considered more closely as follows, with the help of detailed explanations referring to the attached drawings.

DETAILED DESCRIPTION OF THE INVENTION

Figure 1:
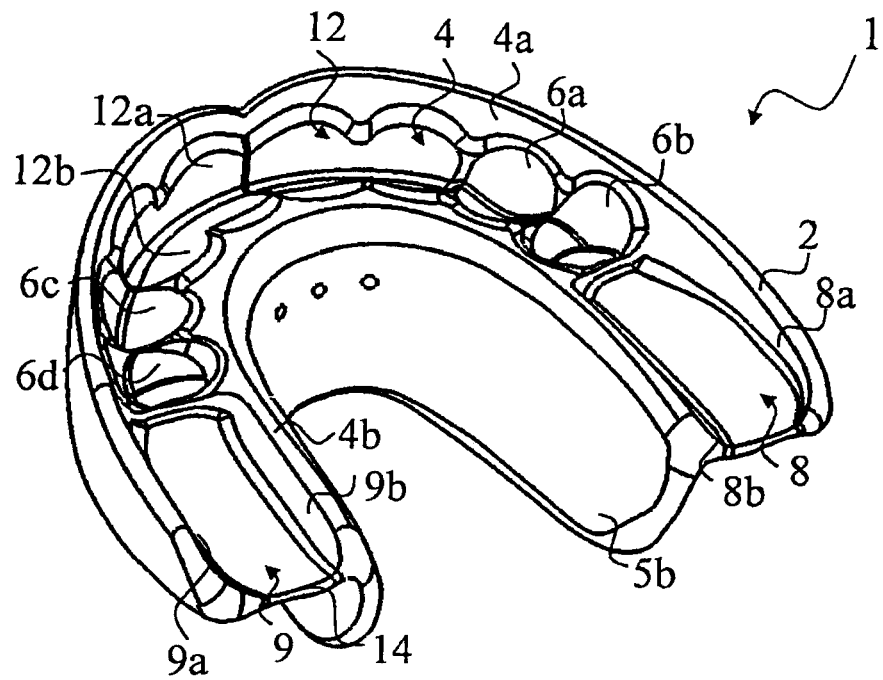
FIG. 1 shows in perspective view the upper jaw side of one occlusion guidance appliance according to the invention.

An occlusion guidance appliance according to the presented invention consists of a U-shaped arch 1, made of elastic and suitably flexible material such as thermoplastic elastomer, plasticized (softened) plastic or rubber, and is roughly shaped like a horseshoe. Accordingly, its shape corresponds at least mainly to the dental arch of the patient. The occlusion guidance appliance has an upper surface 2 and a lower surface 3, of which the upper surface 2 includes the formation of receptive concaves 4 for the teeth of the upper jaw. Equivalently, the lower surface 3 includes a formation of concaves 5 for the teeth of the lower jaw. They are at least sufficiently wide and deep to be able to fit the teeth of the patient at least for the mainly visible parts. Their edges do not necessarily completely extend beyond the gum line. The walls of the concaves form the upper and lower side outer walls 4a and 5a on the side of the lips and correspondingly on the side of the cheeks, and in relation to these from the upper and lower side inner walls 4b and 5b on the opposite sides on the tongue side.

Figure 2:
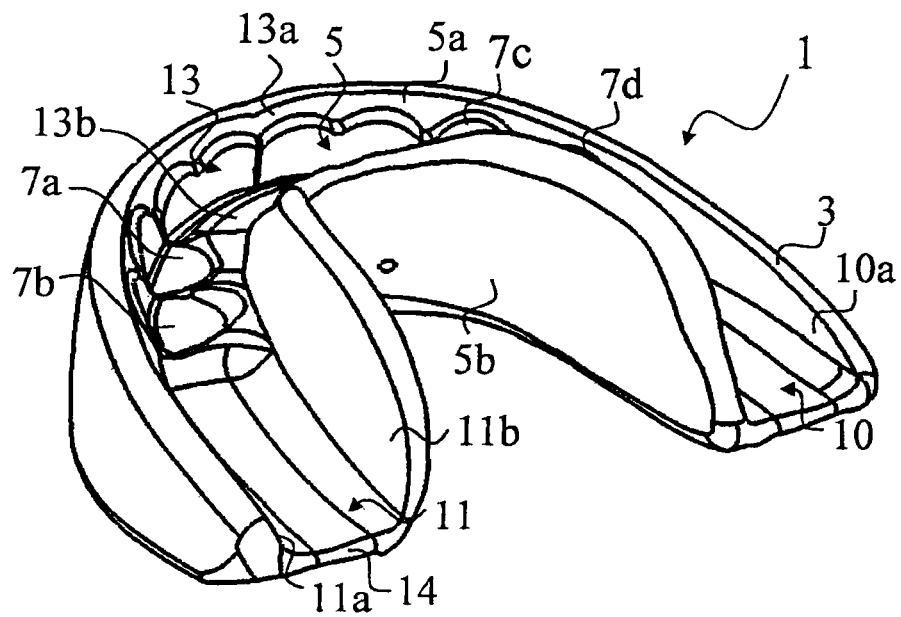
FIG. 2 shows in perspective view the lower jaw side of one occlusion guidance appliance according to the invention.

As FIGS. 1 and 2 show, the bottoms of concaves 4 and 5 are formed by the isthmus 14 separating the concaves, in which hollows have been formed, that is, blanks 6a-6d; 7a-7d for the canine teeth and the first premolars. The thickness of isthmus 14 can be only 1 mm, but according to the advantageous embodiments of the invention it is significantly thicker than this, even 10 mm. By arranging the canine teeth and first premolars in their own blanks, the device can be positioned precisely enough in the mouth of the patient, even though the device contains uniform and common spaces for the other teeth groups.

The hollows of a device according to FIGS. 1-4 extending to the back teeth consist of uniform compartments 8, 9, 10 and 11, which start from the second premolar and continue towards the molars at least to the area where the second permanent molar will erupt. Advantageously, the uniform compartment totally covers the area of the second permanent molar. The compartment can in principle be continued beyond this point, but in practice it has been noted that the device will function fully satisfactorily if space is arranged for three teeth, namely the second premolar and the first and second molar. Extended devices are usually not as comfortable as the devices shown in the drawings, which end in the second molar.

According to the preferred embodiments of the invention, the side walls 4a, 4b, 5a and 5b of these uniform, continuous compartments 8-11 are formed equivalently of the outer and inner walls 8a, 8b and 9a, 9b, 10a, 10b and 11a, 11b, which have significantly straight or slightly curved walls lengthways. On the inner surface, the walls are smooth in such a way that they have not been significantly profiled with tooth forms. Compartments 8-11 are thus shaped like continuous open troughs, the troughs being open from the molar-side end. Seen from above, the compartments are roughly shaped like rectangles.

The outer and inner walls of compartments 8-11, marked in FIGS. 1 and 2 with reference numbers 8a, 8b, 9a, 9b, 10a and 11a, slightly taper towards the edges ending up at the rounded edge. The upper side walls 8a and 9a rise in the front area of the dental arch at least to the gum line and are otherwise higher than the inner side walls 8b and 9b. As graphic 1 shows, the elevation of the device upper outer wall 8a and 9a continues at least significantly in the same direction with the other wall surface. Advantageously, the outer walls 8a and 9a can cover the gum line at least in the area of the first and second tooth, preferably in the area of the third and even the fourth tooth. With the presented solution the risk that the front upper jaw teeth erupt over the edge of the device can be avoided or at least significantly reduced. The rising of the front wall 4a (8a, 9a) thus guides the upper front teeth to erupt inside the concave and at the same time the device will remain more comfortably in the mouth. According to the size of the dental arch, this outer wall extends to at least about 5 mm, typically approximately and even over 10 mm, of the distance of the mentioned isthmus 14 and, thus, depending on the isthmus thickness used, even to about 15 mm of distance from the middle level of isthmus 14.

As explained below in more detail, the inner side wall 5b on the lower surface of the device has been continued downwards towards the base of the mouth cavity. The form of this side wall 5b at the point 10 and 11b of the molar compartments is slightly different from that of the other walls, as its walls are at least essentially evenly thick and taper only near the edge. In the area of the front teeth, the wing turns more strongly away from the teeth and it has been narrowed suitably below the teeth, at the point of the gum, which improves the use comfort (preventing the vomit reflex). From the cross-section of FIG. 4, these and the other forms of the lower wing come out very clearly.

Figure 4:
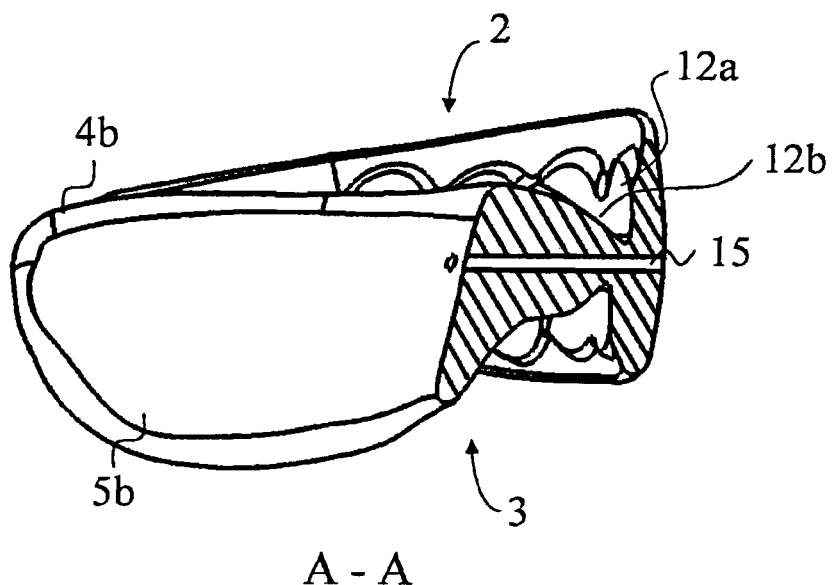
FIG. 4 shows section A-A of FIG. 3.
Figure 5A:
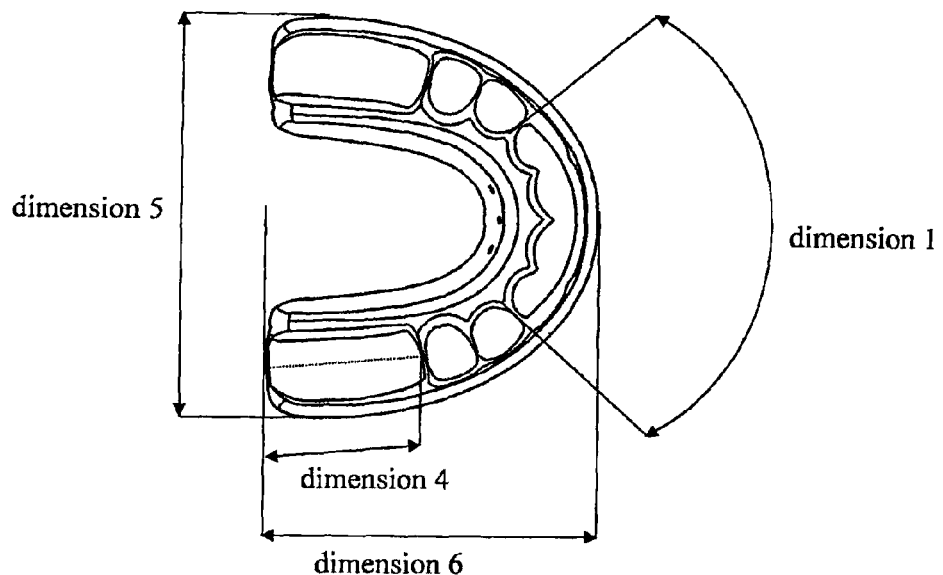
FIGS. 5a and 5b show an upper image of an occlusion guidance appliance according to the invention and respectively an image according to FIG. 3 of device dimensions with measurements.
Figure 5B:
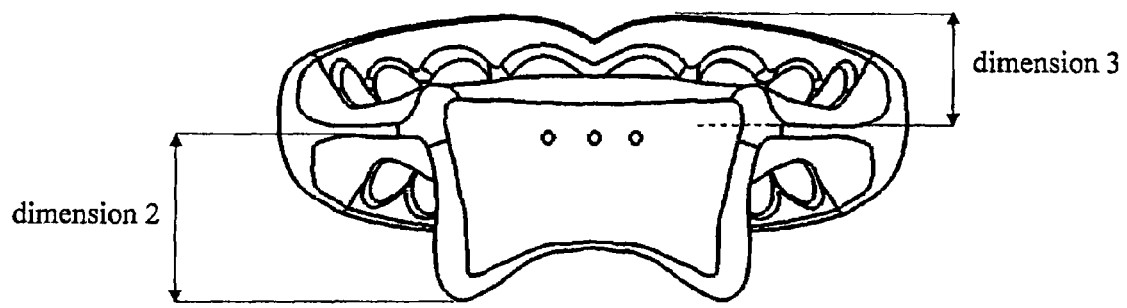

The cross-section of FIG. 4 shows these and the other forms of the lower wing very clearly.

In the device according to FIGS. 1-4, the device has uniform hollows 12 and 13 in the area of the front teeth in the same way as the previously described uniform troughs 8-11 in the molar area. The equivalent walls of these hollows, marked in the graphics and 13 the isthmus 14 between them is mainly even, that is, without any blanks arranged for individual teeth.

Instead, in the walls 12a, 12b, 13a, and 13b, in some embodiments of the invention, it can be foreseen to be arranged not actual clear forms but mainly small lightening features can be arranged in the places of the front teeth.

Seen from above and below, the walls are curved in such a way that they conform to the natural shape of the dental arch. Along the upper edge they can, however, be shaped to follow the teeth. The uniform hollow of the front teeth (first and second teeth) eases the placing of the device in the mouth compared to arranging a blank that is measured for each individual tooth. This is true particularly when the front teeth are twisted.

Figure 3:
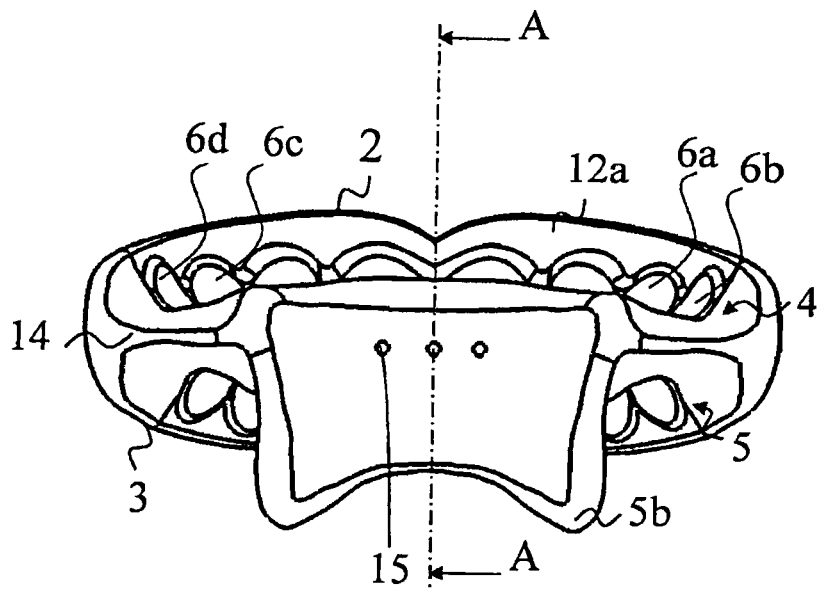
FIG. 3 shows an occlusion guidance appliance according to one embodiment of the invention in relation to its position in anatomical use position viewed from the back side.

FIGS. 3 and 4 show the isthmus 14 separating the upper and lower side concaves 4 and 5. The figures also show how the lower wing formed from the lower tongue-side inner wall 5b extends deepest into the area of the first molar and, moreover, is lower in the area at the front. The isthmus 14 between the upper and lower side compartments 8-11 can be evenly thick or it can be made narrower in the area of the molars, as U.S. Pat. No. 4,830,612 describes. According to one embodiment of the invention, the isthmus 14 in question is thicker in the molar area than elsewhere. This solution aims at correcting open occlusion. More precisely, in this case the otherwise essentially even isthmus has a step at the point between the fourth and fifth teeth each side. According to the invention, when the height of the step in question is of a magnitude of 2-3 mm, this means the minimum isthmus thickness of approximately 1 mm and 3 mm in the front and back teeth area and a maximum of approximately 10 mm and 13 mm, respectively.

In this embodiment, "thickness" refers to the distance between the surfaces that go against the upper and lower teeth.

As stated above, the lower jaw side inner wall 5b of the device has been continued according to the invention to be at least essentially aligned with the surface of the wall in question in such a way that it extends lower in the mouth cavity than the corresponding outer wall in. This inner wall 5b, which is also called "the lower wing" in this application, can advantageously extend, in some parts at least, essentially to the immediate vicinity of the base of the mouth cavity in the area of the first molar.

The lower wing limits the tongue in the surface on the lower jaw side at least sideways, by which means the device more easily remains in place in the patient's mouth, as the following will indicate in more detail. The lower wings keep the lower jaw in place at the front, thus avoiding the drawback of known devices causing lower jaw "dropping", which is explained above in the introduction to the explanation. For their part, the lower wings can also prevent sideways movement of the device, which is affected also by the walls on the cheek-side of the device. In order for the lower wing to fit in the mouth of the patient in the best possible manner, the introduction downwards can be arranged to be smaller at the point of the ligament of the tongue than elsewhere.

In the advantageous application form of the invention, the lower wings have been formed to be slightly curved towards the teeth of the lower jaw, and the edge of the flexible wall follows fairly precisely the shape of the lower jaw arch. In addition, at the front teeth, the starting angle in relation to the vertical plane can be greater than elsewhere, thereby ensuring that it does not press the gum excessively.

FIGS. 1 to 4 show details of the favourable application form of the invention. The cavities 15 formed in the front part of the U-shaped arch in the direction of the sagittal plane can be separately mentioned. The cavities go through the walls of the arch. The cavity holes help breathing, particularly when the patient is sleeping.

The U-shaped arch has been made of silicon polymer or of plasticized polyvinyl chloride. It is particularly advantageous to use liquid silicon as the raw material.

A series can be made of several different-sized devices according to the invention. In the light of the measurements shown in graphics 5a and 5b, this kind of series can contain for example 13 orthodontic activators having the dimensions specified in Table 1. The relative dimensions of the smaller devices intended to be used mainly in the milk tooth phase can be somewhat different from the other devices in the series: Nevertheless, all the devices in the series still contain contours according to the essential characteristics of the invention and (relative) dimensions. The measurements presented in Table 1 are exemplary "approximate" measurements, but they do describe the essential dimensions of the device.

TABLE 1

Typical measurements of one device series according to the invention, formed of different size orthodontic activators

| Device # | 1. Length of upper incisor hollow[1] mm | 2. Lower wing[2] mm | 3. Edge of lip[3] mm | 4. Length of molar compartment[4] mm | | 5. Width of the device mm | 6. Length of the device[6] (depth) mm |
|---|---|---|---|---|---|---|---|
| | | | | upper side | lower side | | |
| 1 | 24 | 8 | 5 | 16 | 19 | 52 | 35 |
| 2 | 25 | 9 | 7 | 18 | 20 | 53 | 38 |
| 3 | 26 | 13 | 10 | 20 | 23 | 55 | 40 |
| 4 | 27 | 13 | 10 | 20 | 23 | 55 | 42 |
| 5 | 28 | 13 | 10 | 20 | 23 | 55 | 42 |
| 6 | 30 | 13 | 10 | 20 | 23 | 56 | 44 |
| 7 | 31 | 14 | 10 | 22 | 24 | 57 | 47 |
| 8 | 32 | 14 | 10 | 22 | 24 | 58 | 47 |
| 9 | 33 | 14 | 10 | 22 | 25 | 60 | 48 |
| 10 | 34 | 14 | 10 | 23 | 26 | 61 | 48 |
| 11 | 35 | 14 | 10 | 23 | 26 | 62 | 48 |
| 12 | 36 | 14 | 11 | 24 | 27 | 63 | 51 |
| 13 | 38 | 16 | 11 | 25 | 28 | 64 | 53 |

[1]Length measured along the bottom of the hollow, essentially along the centre line of the arch formed
[2]Maximum length measured from the surface of the lower molar compartment in the back area
[3]Maximum length of the upper front wall measured approximately between the first and second tooth on the surface of the upper side hollow
[4]Length from the front edge of the molar compartment to its open end
[5]The maximum distance between the molar compartment outer edges
[6]The length between the line connecting the open ends of molar compartments and the front surface of the front wall From Table 1, it can be seen that when talking about devices according to the invention for use by individuals in the changing teeth phase and also by older individuals, the maximum measurement of the lower wing is of a magnitude of about 14 mm and that of the upper side lip edge is about 10 mm—measured from the bottoms of the hollows, that is, always according to the isthmus thickness used, respectively, about 1-6 mm or more measured from the centre point of the masticating surfaces/isthmus.

When the arch of a device in the series, measured along the centre line of the arch and between the second and third tooth, is less than about 26 mm. the maximum distance of the lower edge of the wings to the equivalent point on the surface of the isthmus between the masticating surfaces is approximately 8 to 10 mm, and when the mentioned arch is over 26 mm the mentioned maximum distance is about 14 mm. When the arch is about 32 mm, the length of the compartment starting from the second premolar and terminating in an open end is approx. 22 mm on the upper side and on the lower side approx. 24 mm; and equivalently when the length of the arch is approx. 37 mm, the length in the upper side is approx. 24 mm and in the lower side approx. 27 mm.

Typically, the length of the arch of the smallest device in the series is less than 26 mm and that of the largest device a minimum of 36 mm, preferably at least 38 mm. And when the arch length of the mentioned smallest device, measured along the centre line of the arch and between the second and third tooth, is essentially less than approx. 40 mm, the upper side front wall is at least 5 mm.

A device according to the invention is used for orthodontic treatment in an analogous way, in contrast to the known devices (see for example U.S. Pat. Nos. 4,830,612, 4,799,884 and 4,919,612). In the method, a suitable occlusion guidance appliance device is chosen for each individual from previously described series of devices. Thus, first the length of the dental arch on the upper jaw side is measured—either between the second and third tooth or between the third and the fourth tooth—and a suitable sized device is chosen from the series formed of devices according to the invention on the basis of the measurement. The measurement is taken along the outer surface of the anatomy (the dental arch), and the arch measurement of a suitable device is 1-2 mm smaller than this as it is based on the measurement defined along the base of the isthmus. Selecting the device is thus solely based on the size of the jawbone and a new device is taken into use only on the basis of how the jawbone will grow, independent of how the teeth have otherwise developed.

The device selected is used by biting it actively between the teeth. A method according to the invention can particularly be applied and the device used already at the milk tooth phase and continued with equivalent but larger devices even after the permanent teeth have erupted, in order to guide the teeth to grow and position themselves to achieve a desired, pre-defined occlusion. The device can be used until the permanent teeth have fully erupted and when necessary use can be continued by treatment aiming at maintaining the resulting positioning. Typically, the use of the device can be started approximately at the age of five years, and correspondingly stopped at the age of around 15. In some special cases, use can be continued even to near the age of 20. The device is used always when sleeping and, when necessary, also during the daytime. Compared to a device according to a U.S. Pat. No. 4,830,612, a "changing teeth" device according to the invention presented is longer than the corresponding known device, and thus the device can be used also after the second molar has erupted. The lower wings guide the patient to bite the device correctly. This reduces device breakage. The lower wings help to keep the device in the mouth and functioning in the right way.

Even though it was emphasized earlier that the invention guides occlusion, it is clear that a device according to the invention can—always depending on the situation—position at least a number of the individual's teeth, or guide them to the pre-determined place or position. This need is served particularly by the blanks formed for the individual teeth.

The invention claimed is:

1. An orthodontic device for guiding occlusion of an individual, said device comprising:
   a generally U-shaped arch made of flexible material and configured for extending to molar areas of a dental arch,
   an isthmus separating the device into generally U-shaped concaves on both the lower and upper jaw side of the device, said concaves including outer and inner walls,
   the concaves being structured and arranged for receiving individual's teeth, wherein
   within the molar areas or a part of the molar areas, the inner wall of the concave on the lower jaw side is configured to extend downwards and curve towards the concave so as to essentially follow the shape of the lower jaw and to form a lower wing, which extends from the isthmus of the concave on the lower jaw side towards the base of the mouth cavity, to a distance from 8 mm up to 16 mm.

2. An orthodontic device according to claim 1, wherein said concaves contain uniform compartments that begin from a second premolar and continue towards molars at least partly to an area where the second permanent molar erupts.

3. An orthodontic device according to claim 2, wherein said compartments are shaped like continuous troughs being open at their molar side ends.

4. An orthodontic device according to claim 1, wherein containing within an area of front teeth recesses whose surface walls are essentially smooth.

5. An orthodontic device according to claim 1, wherein said concaves comprise blanks for canines and first premolars.

6. An orthodontic device according to claim 1, wherein said isthmus separating the concaves is thicker at least in an area of molars than in an area of front teeth.

7. An orthodontic device according to claim 6, wherein said isthmus thickness changes stepwise at points between the premolars.

8. An orthodontic device according to claim 6, wherein said isthmus is essentially even and its thickness in the molar area is essentially constant within the range of 3-13 mm and, respectively, its thickness within the thinner area essentially constant within the range of 1-10 mm.

9. An orthodontic device according to claim 1, wherein the walls of the concaves are formed by the outer walls on the labial side or on the buccal side, respectively, and by the inner walls on the opposite sides of the concaves on the lingual side such that the inner wall on the lower jaw side extends downwards lower than the corresponding outer wall.

10. An orthodontic device according to claim 1, wherein said lower wing has been arranged to reach the immediate proximity of the base of the mouth cavity.

11. An orthodontic device according to claim 1, wherein at the point of the ligament of a tongue, the extent to which said lower wing extends towards the bottom of the mouth cavity has been reduced.

12. An orthodontic device according to claim 1, wherein said lower wing extends at the point of the first molar to a maximum distance of 14 mm from the lower jaw side surface of said isthmus and to a distance of 3 to 6 mm in the area of the ligament of the tongue.

13. An orthodontic device according to claim 1 wherein the outer wall on the upper jaw side has been at least partially continued upwards to extend above a gum line.

14. An orthodontic device according to claim 13, wherein said upper side outer wall extends essentially above the gum line in areas of first and second teeth, in areas of first, second, third and fourth teeth.

15. An orthodontic device according to claim 13 wherein said outer wall on the upper jaw side extends at its highest point to 10 mm distance from of the upper jaw side surface of said isthmus.

16. An orthodontic device according to claim 1, the device comprising compartments starting from second premolars and terminating open at their ends, wherein length of the arch of the isthmus on the upper jaw side between the second and third teeth as measured along the center line of the arch is 32 mm and lengths of said compartments are 22 mm on the upper side and 24 mm on the lower side.

17. An orthodontic device according to claim 1, the device comprising compartments starting from second premolars and terminating open at their ends, wherein length of the arch of the isthmus on the upper jaw side between the second and third teeth as measured along the center of the arch line is approx. 37 mm and length of said compartment is 24 mm on the upper side and 27 mm on the lower side.

18. An orthodontic device according to claim 1, wherein said lower wing extends to its maximum distance from the lower jaw side surface of said isthmus at points of first molars.

\* \* \* \* \*